US007605290B2

(12) United States Patent
Niddam-Hildesheim et al.

(10) Patent No.: US 7,605,290 B2
(45) Date of Patent: Oct. 20, 2009

(54) PROCESSES FOR THE SYNTHESIS OF O-DESMETHYLVENLAFAXINE

(75) Inventors: Valerie Niddam-Hildesheim, Kadima (IL); Natalia Shenkar, Petach Tiqva (IL); Sharona Shachan-Tov, Kfar-Saba (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/881,731

(22) Filed: Jul. 26, 2007

(65) Prior Publication Data

US 2008/0139849 A1 Jun. 12, 2008

Related U.S. Application Data

(60) Provisional application No. 60/833,616, filed on Jul. 26, 2006, provisional application No. 60/837,879, filed on Aug. 14, 2006, provisional application No. 60/849,216, filed on Oct. 3, 2006, provisional application No. 60/843,998, filed on Sep. 11, 2006, provisional application No. 60/849,255, filed on Oct. 3, 2006, provisional application No. 60/906,639, filed on Mar. 12, 2007, provisional application No. 60/906,879, filed on Mar. 13, 2007.

(51) Int. Cl.
*C07C 209/00* (2006.01)
*C07C 211/00* (2006.01)

(52) U.S. Cl. ....................... 564/409; 564/336
(58) Field of Classification Search ................ 564/336, 564/409
See application file for complete search history.

(56) References Cited

U.S. PATENT DOCUMENTS

| | | | |
|---|---|---|---|
| 4,535,186 | A | 8/1985 | Husbands et al. |
| 6,197,828 | B1 | 3/2001 | Jerussi et al. |
| 6,673,838 | B2 | 1/2004 | Hadfield et al. |
| 6,689,912 | B2 | 2/2004 | Weber |
| 7,026,508 | B2 | 4/2006 | Winkley et al. |
| 2002/0120164 | A1 | 8/2002 | Chavan et al. |
| 2003/0045583 | A1 | 3/2003 | Hadfield et al. |
| 2004/0106818 | A1 | 6/2004 | Zhiyin et al. |
| 2004/0181093 | A1* | 9/2004 | Kim et al. ................ 564/415 |
| 2005/0096479 | A1 | 5/2005 | Hadfield et al. |
| 2005/0197392 | A1 | 9/2005 | Jerussi et al. |
| 2007/0135449 | A1 | 6/2007 | Mahaney et al. |

FOREIGN PATENT DOCUMENTS

| | | |
|---|---|---|
| EP | 0 112 669 A2 | 7/1984 |
| EP | 1 219 591 B1 | 7/2002 |
| GB | 2 173 787 A | 10/1986 |
| WO | WO 00/32555 A1 | 6/2000 |
| WO | WO 00/59851 A1 | 10/2000 |
| WO | WO 02/064543 A2 | 8/2002 |
| WO | WO 03/000652 A1 | 1/2003 |
| WO | WO 03/048104 A1 | 6/2003 |
| WO | WO 2005/049560 A2 | 6/2005 |
| WO | WO 2007/000294 A1 | 1/2007 |
| WO | WO 2007/005961 A | 1/2007 |
| WO | WO 2007/011594 A2 | 1/2007 |
| WO | WO 2007/067501 A1 | 6/2007 |
| WO | WO2007/071404 | 6/2007 |
| WO | WO 2007/120923 A1 | 10/2007 |
| WO | WO2007147564 * | 12/2007 |
| WO | WO 2008/015584 A2 | 2/2008 |

OTHER PUBLICATIONS

Klamerus, K.J. et al., "Introduction of the Composite Parameter to the Pharmokinetics of Venlafaxine and its Active O-Desmethyl Metabolite," J. Clin. Pharmacol. (1992) vol. 32(8), pp. 716-724.
International Search Report of Application No. PCT/US2007/017011, dated Feb. 5, 2008.
Yardley, John P., et al., 2-Phenyl-2-(1-hydroxycycloalkyl)ethylamine Derivatives: Synthesis and Antidepressant Activity, J. Med. Chem. (1990) 33, pp. 2899-2905, XP000891765.
Cheng, Guohou et al., "Process for preparing 1-[2-(2-(dimethylamino)-1-(4-methoxyphenyl)ethyl]cyclohexanol hydrochloride," Database CA [Online] Chemical Abstracts Service, Columbus, Ohio, US; XP002466013 retrieved from STN Database accession No. 133:252074 abstract & CN 1 240 206 A (Huadong Science and Engineering Univ., Peop. Rep. China, Jan. 5, 2000).
Chavan, S.P., et al., "An efficient and green protocol for the preparation of cycloalkanols: a practical synthesis of venlafaxine," Tetrahedron Letters (2004) vol. 45, pp. 7291-7295, XP002419152.

* cited by examiner

*Primary Examiner*—Jafar Parsa
(74) *Attorney, Agent, or Firm*—Kenyon & Kenyon LLP

(57) ABSTRACT

The present invention describes processes for the preparation of O-desmethylvenlafaxine and tridesmethylvenlafaxine, which may be used as an intermediate in preparing O-desmethylvenlafaxine.

32 Claims, No Drawings

PROCESSES FOR THE SYNTHESIS OF O-DESMETHYLVENLAFAXINE

CROSS REFERENCE TO RELATED APPLICATIONS

The present application claims the benefit of the following U.S. Provisional Patent Application Nos.: 60/833,616, filed Jul. 26, 2006; 60/837,879, filed Aug. 14, 2006; 60/849,216, filed Oct. 3, 2006; 60/843,998, filed Sep. 11, 2006; 60/849,255, filed Oct. 3, 2006; 60/906,639, filed Mar. 12, 2007; and 60/906,879, filed Mar. 13, 2007. The contents of these applications are incorporated herein by reference.

FIELD OF THE INVENTION

The invention encompasses a process for the synthesis of O-desmethylvenlafaxine and a novel intermediate, tridesmethyl venlafaxine.

BACKGROUND OF THE INVENTION

Venlafaxine, (±)-1-[2-(Dimethylamino)-1-(4-ethyoxyphenyl)ethyl]cyclo-hexanol is the first of a class of anti-depressants. Venlafaxine acts by inhibiting re-uptake of norepinephrine and serotonin, and is an alternative to the tricyclic anti-depressants and selective re-uptake inhibitors. Venlafaxine has the following chemical formula, Formula I:

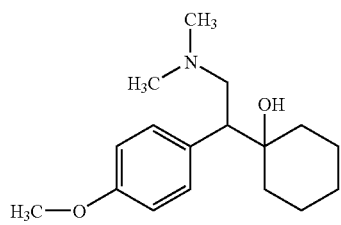

Formula I

O-desmethylvenlafaxine, 4-[2-(dimethylamino)-1-(1-hydroxycyclohexyl)ethyl]phenol, is a major metabolite of venlafaxine and has been reported to inhibit norepinephrine and serotonin uptake. See Klamerus, K. J. et al., "Introduction of the Composite Parameter to the Pharmacokinetics of Venlafaxine and its Active O-Desmethyl Metabolite," *J. Clin. Pharmacol.* 32:716-724 (1992). O-desmethylvenlafaxine has the following chemical formula, Formula II:

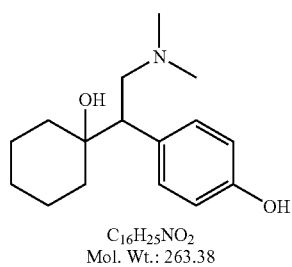

Formula II $C_{16}H_{25}NO_2$
Mol. Wt.: 263.38

Processes for the synthesis of O-desmethylvenlafaxine, comprising a step of demethylation of the phenol group of venlafaxine, are described in U.S. Pat. Nos. 7,026,508 and 6,689,912, and in U.S. publication No. 2005/0197392, which are incorporated herein by reference.

The synthesis disclosed in the above references is performed according to the following scheme:

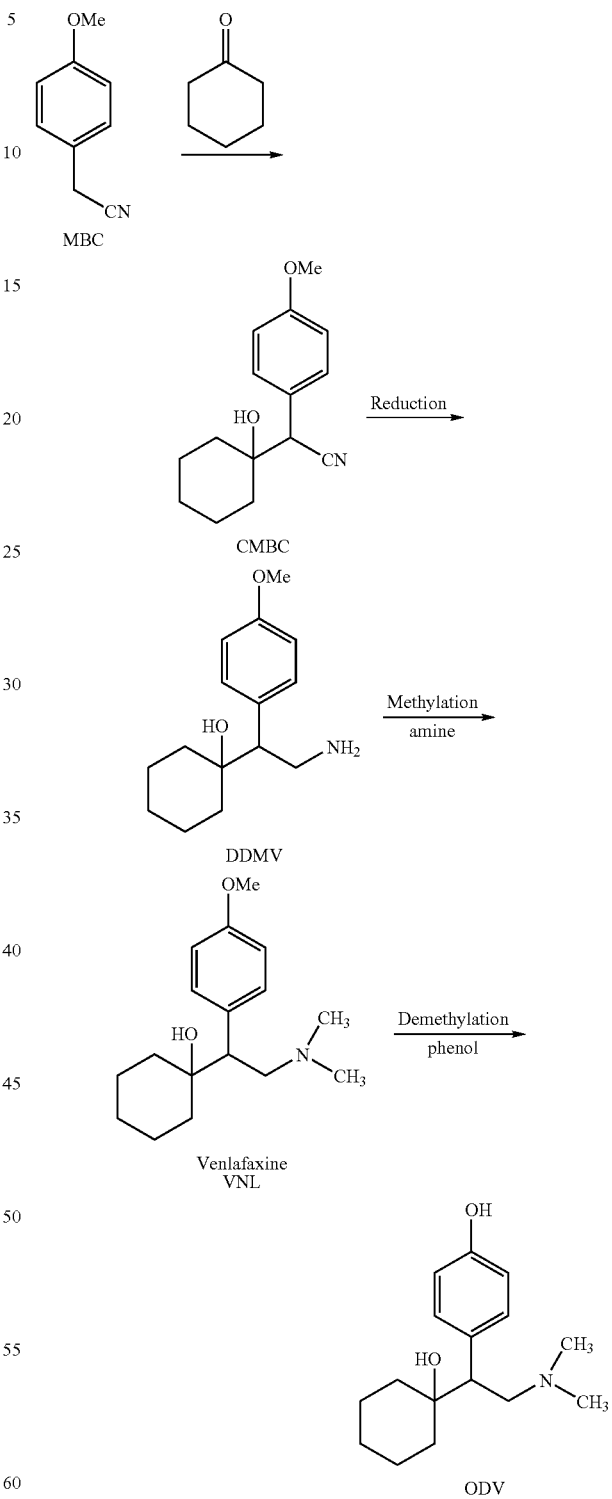

"MBC" refers to methyl benzyl cyanide, "CMBC" refers to cyclohexyl methylbenzyl cyanide, "DDMV" refers to didesmethyl venlafaxine, and "ODV" refers to O-desmethylvenlafaxine.

However, the processes disclosed in the above US patents and US patent applications all remain problematic when applied to industrial scale production. The process in U.S. Pat. No. 7,026,508 uses L-selectride, a compound which is very problematic when scaling up the process for industrial application. Further, the process disclosed in US Application Publication No. 2005/0197392 uses lithiumdiphenyl phosphine, a compound which handling and use in industrial scale processes is extremely dangerous. Also, the process disclosed in U.S. Pat. No. 6,689,912 uses methanol as a solvent, which use is problematic when traces of methanol remain and in subsequent process steps when high temperatures are applied.

Therefore, there is a need in the art for a new synthetic route for obtaining O-desmethylvenlafaxine, using a precursor of venlafaxine to directly obtain O-desmethylvenlafaxine.

SUMMARY OF THE INVENTION

In one embodiment, the invention encompasses tridesmethyl venlafaxine.

In another embodiment, the invention encompasses a process for preparing tridesmethyl venlafaxine comprising demethylating didesmethylvenlafaxine to obtain tridesmethylvenlafaxine. The process of demethylating didesmethylvenlafaxine preferably comprises: combining didesmethylvenlafaxine, a solvent, and a sulfide containing demethylating agent to form a mixture, heating the mixture, and optionally recovering tridesmethyl venlafaxine from the mixture.

In another embodiment, the present invention provides a process for preparing O-desmethylvenlafaxine comprising demethylating didesmethylvenlafaxine to obtain tridesmethyl venlafaxine, and converting said tridesmethyl venlafaxine to O-desmethylvenlafaxine.

In another embodiment, the present invention provides a process for preparing O-desmethylvenlafaxine comprising reductive amination of tridesmethylvenlafaxine to obtain O-desmethylvenlafaxine. The process of reductive amination of tridesmethylvenlafaxine preferably comprises: combining a solution of tridesmethyl venlafaxine and a formaldehyde source with a reducing agent, preferably sodium borohydride, sodium triacetoxy borohydride, or sodium cyanoborohydride, to obtain a reaction mixture, and recovering the O-desmethylvenlafaxine from the reaction mixture.

In another embodiment, the present invention provides a process for preparing O-desmethylvenlafaxine comprising selectively N,N methylating tridesmethylvenlafaxine to obtain O-desmethylvenlafaxine. The process of selectively N,N methylating tridesmethylvenlafaxine preferably comprises: combining tridesmethyl venlafaxine, an organic solvent, and a methylating agent to form a mixture, and recovering the O-desmethylvenlafaxine from the mixture.

DETAILED DESCRIPTION OF THE INVENTION

The embodiment of the invention encompasses a new synthetic route for obtaining O-desmethylvenlafaxine directly from a venlafaxine intermediate.

In a process according to the invention, the methoxy group of didesmethyl venlafaxine ("DDMV"), its chemical name being 1-[2-amino-1-(4-methoxyphenyl)ethyl]cyclohexanol, is demethylated to form the intermediate tridesmethyl venlafaxine ("TDMV"), its chemical name being 4-[2-amino-1-(1-hydroxycyclohexyl)ethyl]phenol. The intermediate TDMV is then subjected to reductive amination or selective N,N methylation to produce O-desmethylvenlafaxine ("ODV"), as described in the following scheme:

wherein "TDMV" refers to the novel intermediate tridesmethyl venlafaxine.

As used herein the term "room temperature" means the ambient temperature of an typical laboratory, which is usually about that of Standard Temperature and Pressure (STP).

As used herein the term "increased pressure" refers to a pressure above 1 atmosphere as is commonly understood by one of skill in the art. Conversely, as used herein, the term "reduced pressure" means a pressure of below 1 atmosphere as commonly understood by one of skill in the art.

As used herein, the term "substantially pure" means a compound of very high purity as is understood by one of skill in the art such as for example a purity of at least 95% by HPLC area percent.

As used herein, an "isolated" compound means the compound has been separated from the reaction mixture in which it was formed.

In one embodiment, the present invention provides tridesmethyl venlafaxine, chemically named 4-[2-amino-1-(1-hydroxycyclohexyl)ethyl]phenol and having the following Formula III:

Formula III tridesmethyl venlafaxine

The tridesmethyl venlafaxine or salts thereof as in the present invention may have a purity of 75% by HPLC area percent or higher. Preferably, tridesmethyl venlafaxine or its salt is substantially pure, more preferably at least 95% pure by HPLC area percent, most preferably at least 98% pure by HPLC area percent.

In one embodiment tridesmethyl venlafaxine is prepared by demethylating didesmethyl venlafaxine to obtain tridesmethylvenlafaxine. Demethylation of disdesmethylvenlafaxine may be carried out by reacting didesmethyl venlafaxine with a sulfide containing demethylating agent. This reaction comprises maintaining a mixture of didesmethylvenlafaxine and the sulfide containing demethylating agent at an elevated temperature for a sufficient time to form tridesmethyl venlafaxine.

As used herein, the term "elevated temperature" means a temperature greater than about 50° C., but less than a temperature at which about 10% or more of either the reactants or the product degrades over the course of the reaction. Preferably, the elevated temperature at which the demethylating reaction of the process of the present invention is carried out is from about 100° C. to about 300° C., more preferably from about 120° C. to about 250° C., even more preferably from about 140° C. to about 210° C., at atmospheric pressure. Alternatively, the demethylating reaction of didesmethylvenlafaxine in the presence of a sulfide containing demethylating agent may be carried out a correspondingly lower temperature under increased pressure.

Preferably, tridesmethyl venlafaxine may be prepared by a process comprising combining didesmethylvenlafaxine, a solvent, and a sulfide containing demethylating agent to form a mixture, heating the mixture, and optionally recovering tridesmethyl venlafaxine from the mixture.

A suitable solvent for use in the above process may be a high boiling point solvent, particularly when the process is carried out at atmospheric pressure. The term "high boiling point solvent" is used and understood by one of ordinary skill in the art and refers to a solvent having a boiling point higher than about 100° C. Preferably, the high boiling point solvent is selected from the group consisting of: toluene, dimethylformamide ("DMF"), dimethylsulfoxide ("DMSO"), N-methyl-2-pyridone, N-methyl-2-pyrrolidone (NMP), 1-methyl-2-pyrrolidinone, dimethylacetamide ("DMA"), polyethylene glycol, Marlotherm, silicon oil, N,N'-dimethylpropyleneurea ("DMPU"), dimethylolethyleneurea ("DMEU"), Hexamethylphosphoramide ("HMPA"), diethylformamide ("DEF"), diethyleneamine ("DEA"), morpholine, sulfolane, phenylether and mixtures thereof. More preferably, the high boiling point solvent is polyethylene glycol, NMP or DMA.

Preferably, the didesmethyl venlafaxine starting material is didesmethyl venlafaxine free base, which can be obtained by any method known to the skilled artisan, such as described in U.S. Pat. No. 7,026,508 and U.S. Pat. No. 6,689,912, herein incorporated by reference, or by conversion of the commercially available salt to the free base form. Such conversion may comprise dissolving a commercially available salt of didesmethylvenlafaxine, such as a hydrochloride salt or acetate salt thereof, in an organic solution, preferably a $C_{1-4}$ alcohol such as methanol, and adding a base such as for example sodium hydroxide to the solution. The didesmethylvanlafaxine free base may then be recovered, for example, by evaporation of the solvent. Alternatively, a salt of didesmethylvenlafaxine may be used as starting material without prior conversion to the free base. The free base of didesmethyl venlafaxine may then be prepared in situ by the addition of a base.

The sulfide containing demethylating agent is selected from metal sulfides, having either a valence of −1 or −2, thiolates and thiols. Preferably, the demethylating agent is a mercaptan or a salt thereof, a salt of a thioalcohol, or sodium sulfide. A preferred thiolate is a high molecular weight thiolate or arene thiolate. More preferably, the sulfide containing demethylating agent is sodium dodecanethiolate or thiophenol. The sodium dodecanethiolate can be obtained by any method known to the skilled artisan, such as combining sodium methoxide, methanol and dodecanethiol.

Whenever thiophenol is used, a base catalyst is preferably employed in the reaction mixture. Preferably, the base catalyst is a metal carbonate, hydride, hydroxide, amide or oxide. More preferably the base catalyst is selected from the group consisting of $K_2CO_3$, $Li_2CO_3$, $Na_2CO_3$, $Cs_2CO_3$, $MgCO_3$, $CaCO_3$, $BaCO_3$, $SrCO_3$, $ZnCO_3$, $NaHCO_3$, $KHCO_3$, $LiOH$, $NaOH$, $CsOH$, $LiH$, $NaH$, $KH$, $CaH_2$, $LiNH_2$, $NaNH_2$, and tBuOK, most preferably potassium carbonate.

Preferably, the mixture is heated to a temperature of about 100° C. to about 300° C., preferably of about 140° C. to about 210° C., preferably of about 155° C. to about 190° C., at atmospheric pressure. The reaction mixture may be heated to a temperature of about 50° C. to about 200° C., preferably about 80° C., whenever the demethylating reaction is carried out under pressure (increased pressure). Under pressure, the reaction may be carried out an increased pressure of more than 1 atmosphere, preferably at a pressure between about 1 bar to about 10 bar. The mixture is heated for a sufficient period of time to obtain the tridesmethylvenlafaxine, preferably for a period of about 1 hour to about 12 hours, more preferably of about 2 hours to about 6 hours, even more preferably for a period of about 2.5 hours to about 5.5 hours.

The tridesmethyl venlafaxine may be recovered from the mixture by any method known to the skilled artisan. In one embodiment, recovery of tridesmethylvenlafaxine from the mixture comprises the steps of cooling the mixture; slurrying the obtained cooled mixture, preferably by adding silica; filtering and washing the slurry with a $C_1$-$C_4$ alcohol, preferably isopropanol; suspending the slurry in a $C_1$-$C_4$ alcohol, preferably isopropanol, and adjusting the pH to pH 8; filtering the suspension; and evaporating the solvent from the filtrate.

In order to yield an even purer product, TDMV recovered as described above may then be slurried in water at ambient temperature for about 10 minutes to about 24 hours, preferably about 2 hours, preferably followed by removal of the water and preferably washing of the obtained product with water. TDMV so obtained is then preferably filtered and dried to yield crystalline TDMV. Optionally, the slurry may be cooled to about 0° C.

In another embodiment, the present invention provides a process for preparing O-desmethylvenlafaxine comprising demethylating didesmethylvenlafaxine to obtain tridesmethyl venlafaxine, and converting said tridesmethyl venlafaxine to O-desmethylvenlafaxine.

In another embodiment, the present invention provides a process for preparing O-desmethylvenlafaxine or a salt thereof comprising reductive amination of tridesmethylvenlafaxine to obtain O-desmethylvenlafaxine. The process of reductive amination of tridesmethylvenlafaxine preferably comprises: combining a solution of tridesmethyl venlafaxine and a formaldehyde source with a reducing agent to obtain a reaction mixture and recovering the O-desmethylvenlafaxine from the reaction mixture.

The tridesmethyl venlafaxine starting material may be provided in a solution with a suitable solvent, preferably an organic solvent such as $C_{1-4}$ alcohol, preferably methanol or isopropanol, or a $C_{1-6}$ carboxylic acid, preferably acetic acid or formic acid, or $C_6$-$C_8$ aromatic hydrocarbons, preferably toluene, or $C_3$-$C_5$ ketones, preferably acetone and mixtures thereof. Additional solvents that can be used are also NMP and DMF. Alternatively, the suitable solvent can be water.

Optionally, the process is performed under acidic conditions. If the solvent used is not already acidic, an inorganic acid, such as HCl, or organic acid is added, preferably a $C_{1-6}$ carboxylic acid, more preferably formic acid or an acetic acid.

The desired N,N-dimethylation of tridesmethylvenlafaxine may be carried out using an aldehyde, a preferred aldehyde being formaldehyde. Any source of formaldehyde can be used, such as gaseous formaldehyde, paraformaldehyde ("paraform"), a formalin solution, and trioxane to mention just a few of those known to one of ordinary skill in the art.

A suitable reducing agent is selected from the group consisting of sodium borohydride, sodium triacetoxy borohydride, and sodium cyanoborohydride. Prior to combining the reducing agent, the solution may be cooled to a temperature of less than about 10° C., preferably less than about 5° C., more preferably to a temperature between about 0° C. and about 5° C.

The O-desmethylvenlafaxine may be recovered from the reaction mixture by any method known to the skilled artisan.

In another embodiment, the present invention provides a process for preparing O-desmethylvenlafaxine comprising selectively N,N methylating tridesmethylvenlafaxine to obtain O-desmethylvenlafaxine. The process of selectively N,N methylating tridesmethylvenlafaxine preferably comprises: combining tridesmethyl venlafaxine and a methylating agent, preferably with an organic solvent, to form a mixture, and recovering the O-desmethylvenlafaxine from the mixture.

A preferred organic solvent is selected from the group consisting of dichloromethane, dimethylsulfoxide, acetonitrile, tetrahydrofuran, diethylether, and hexane.

Optionally, the process is performed under basic conditions. Preferably, the source for providing basic reaction conditions may be selected from the group consisting of butyllithium, triethylamine, and sodium hydride.

A preferred methylating agent is selected from the group consisting of a methyl halide, preferably methyl iodide, and dimethylsulfate.

The reaction may be carried out for a period of time sufficient to obtain O-desmethylvenlafaxine. A "sufficient" amount of time depends in part on the desired extent of reaction and the reaction conditions, such as temperature. One of ordinary skill in the art can easily monitor the reaction to determine when a sufficient amount of time has transpired. The preferred amount of time is generally about 30 minutes to about 24 hours, preferably about 18 hours.

The O-desmethylvenlafaxine may be recovered from the mixture by any method known to the skilled artisan.

Having described the invention with reference to certain preferred embodiments, other embodiments will become apparent to one skilled in the art from consideration of the specification. The invention is further defined by reference to the following examples describing in detail the synthesis of the compound tridesmethyl venlafaxine and further its conversion to O-desmethylvenlafaxine. It will be apparent to those skilled in the art that many modifications, both to materials and methods, may be practiced without departing from the scope of the invention.

EXAMPLES

Example 1

Determining the Purity/Impurity Profile of Tridesmethyl Venlafaxine and O-Desmethylvenlafaxine by HPLC

| HPLC | |
|---|---|
| Column & Packing: | Zorbax SB C-18 4.6*250 mm Part No. 28105-020 or equivalent column |
| Column Temperature: | 25° C. |
| Buffer | Add 4.0 ml of trifluoroacetic acid and 7.0 ml of triethylamine to 1 L of water adjust the pH to 3.0 with triethylamine. |
| Eluent: | |
| Reservoir A | 30% Acetonitrile and 70% Buffer |
| Reservoir B | To a mixture of 700 ml Acetonitrile and 300 ml buffer add 1.6 ml of trifluoroacetic acid and 2.9 ml of triethylamine measure the pH it should be about 3.0 (correct the pH with triethylamine or trifluoroacetic acid if necessary). |
| Gradient | Time　　　　　Reservoir A　　　　Reservoir B |
|  | 0　　　　　　100%　　　　　　0% |
|  | 21 min　　　　100%　　　　　　0% |
|  | 55 min　　　　45%　　　　　　55% |
|  | Equilibrium time: 10 min |
| Flow Rate: | 1.0 ml/min |
| Detector: | 230 nm |
| Sample Volume: | 10 µl |
| Diluent: | Eluent A |

Mobile phase composition and flow rate may be varied in order to achieve the required system suitability.

Sample Preparation

Weigh accurately about 10 mg of sample in a 20 ml amber volumetric flask. Dissolve with eluent A.

Method

Inject the sample solutions into the chromatograph, continuing the chromatogram of sample up to the end of the gradient. Determine the areas for each peak in each solution using a suitable integrator.

Calculation

Impurity Profile Determination $$\% \text{ impurity} = \frac{\text{area impurity in sample}}{\text{Total area}} \times 100$$

Example 2

Preparation of Tridesmethyl Venlafaxine

1) Neutralization of Didesmethylvenlafaxine Hydrochloride ("DDMVxHCl")

DDMVxHCl (5.73 g, 20 mmol) was dissolved in a minimum volume of methanol, and sodium hydroxide (0.88 g, 22 mmol) was added to form a mixture. The mixture was stirred at room temperature for 15 minutes. The solvent was then evaporated under reduced pressure at 90° C.

2) Preparation of Sodium Dodecanethiolate

In another flask, sodium methoxide (1.43 g, 26 mmol) was dissolved in 10 ml methanol, and dodecanethiol (6.5 ml, 27 mmol) was added. The resulting solution was stirred at room temperature for 15 minutes. The solvent was then evaporated under reduced pressure at 90° C.

3) Demethylation

The DDMV free base produced in step 1) was taken in polyethylene glycol ("PEG") 400 (5 ml) and added to the flask containing sodium dodecanethiolate of step 2). Additional PEG 400 (3 ml) was used to wash the flask of step 1). The resulting mixture was heated at 190° C. with a sand bath under nitrogen flow. The internal temperature of the flask reached 155° C. The reaction was monitored by thin layer chromatography ("TLC") and determined to be complete after 2.5 hours.

Example 3

Preparation of Tridesmethyl Venlafaxine

1) Neutralization of Didesmethylvenlafaxine Hydrochloride ("DDMVxHCl")

DDMVxHCl (30 g, 105 mmol) was dissolved in a minimum volume of methanol, and sodium hydroxide (6.24 g, 115 mmol) was added to form a mixture. The mixture was stirred at room temperature for 15 minutes. The solvent was then evaporated under reduced pressure at 90° C. Traces of methanol were evaporated by adding toluene and evaporating it at reduced pressure at 100° C. overnight.

2) Preparation of Sodium Dodecanethiolate

In another flask, sodium methoxide (8.1 g, 150 mmol) was dissolved in 10 ml methanol, and dodecanethiol (32.8 ml, 136.6 mmol) was added. The resulting solution was stirred at room temperature for 15 minutes. The solvent was then evaporated under reduced pressure at 90° C. Traces of methanol were evaporated by adding toluene and evaporating it at reduced pressure at 100° C. for two hours.

3) Demethylation

The DDMV free base produced in step 1) was taken in polyethylene glycol ("PEG") 400 (30 ml) and added to the flask containing sodium dodecanethiolate of step 2). Additional PEG 400 (3 ml) was used to wash the flask of step 1). The resulting mixture was heated at 190° C. with a sand bath under nitrogen flow. The internal temperature of the flask reached 190° C. The reaction was monitored by thin layer chromatography and determined to be complete after 3 hours.

4) Work Up

The reaction mixture was allowed to cool. When the temperature reached 110° C., toluene (100 ml) was added. When the temperature reached room temperature, silica (30 g) was added and the resulting slurry stirred for 1 hour. Then the silica was filtered. The filtrate was determined to contain dodecanethiol (and methyl dodecane thioether) by TLC analysis. The silica, which contained the product, was then suspended in isopropanol (100 mL) to form a slurry. The resulting slurry was stirred at 60° C. for 1 hour. The slurry was then filtered and the filtrate was determined to contain ODV, DDMV, and an impurity. The silica was again suspended in isopropanol (100 ml) and a solution of hydrochloric acid in isopropanol was added until pH=8. The silica was then filtered and the solvent from the filtrate was evaporated to recover pure TDMV, with a purity of 100% by HPLC area percent, yield 52%.

Example 4

Preparation of Tridesmethyl Venlafaxine

DDMVxHCl (2 g, 7 mmol), NaOMe (0.96 g, 17.7 mmol), dodecanethiol (2.3 ml=1.84 g, 9 mmol) and DMA (4 ml) were mixed together and placed in rotovapor under reduced pressure in order to evaporate all traces of MeOH formed during the contact of NaOMe with dodecanethiol and DDMV.HCl. The mixture was then heated in a sand bath at 180° C. ($t_{in}$=135° C.). After 2.5 hours, a sample was analyzed by HPLC, containing 36% TDMV.

Example 5

Preparation of Tridesmethyl Venlafaxine

DDMVxHCl (1 g, 4 mmol), $K_2CO_3$ (0.6 g, 4.4 mmol), thiophenol (0.8 ml, 6 mmol) and NMP (4 ml) were charged in a 50 ml flask and heated in a sand bath. The temperature of the bath was kept at 210° C. for 6 hours. HPLC analysis confirmed full consumption of DDMV. TDMV was obtained with a purity of 83.5% by HPLC area percent.

Example 6

Preparation of Tridesmethyl Venlafaxine

DDMVxHCl (10 g, 40 mmol), $K_2CO_3$ (6 g, 44 mmol), Thiophenol (8 ml, 60 mmol) and NMP (40 ml) were charged in a 250 ml flask equipped with magnetic stirrer, condenser and nitrogen inlet, and heated in a sand bath. The temperature of the bath was kept at 210° C. for 5.5 hours. HPLC analysis confirmed full consumption of DDMV. TDMV was obtained with a purity of 95% by HPLC area percent.

Example 7

Preparation of TDMV from DDMV

1) Neutralization of DDMVxHCl.

DDMVxHCl (10 g, 0.034 mol) was dissolved in MeOH (15 ml), and NaOMe (2.07 g, 0.038 mol) was added. The mixture was stirred at room temperature for 30 minutes, and the solvent evaporated under reduced pressure at 90° C.

2) Demethylation

DDMV free base (prepared in step 1) was taken in NMP (15 ml) and $Na_2S$ (4.3 g, 0.035 mol) was added to 250 ml flask equipped with mechanical stirrer, condenser and nitrogen inlet. The reaction mixture was heated in sand bath to 230° C. and the reaction was monitored by HPLC.

Example 8

Preparation of TDMV Under Pressure

A 250 ml autoclave is charged with 5 g DDMV base (0.020 mol), 4.41 g thiophenol (0.040 mol, 2 eq) and solvent (10 ml) and catalytic amount of $K_2CO_3$. The reaction mixture is stirred from 40° C. to 220° C. and 1-10 bar pressure for 4 h. The mixture is then cooled to room temperature. At ambient temperature solvent (10 ml) and water (10 ml) are added and the product is recovered to obtain TDMV.

Example 9

Preparation of TDMV from DDMV

DDMV.HCl (10 g, 35 mmol), $K_2CO_3$ (5.1 g, 38.4 mmol), Thiophenol (6.2 ml, 52.5 mmol) and NMP (20 ml) were charged in a 100 ml flask equipped with mechanical stirrer, condenser and nitrogen inlet, and were heated in a sand bath. The temperature of the reaction mixture was about 125° C.±10° C. for 4 hours. The reaction mixture was cooled to 90° C. and $H_2O$ (50 ml) was added dropwise inducing precipitation. The slurry was cooled to 25° C. and stirred for about 80 minutes. The solid was filtered, washed with $H_2O$ (20 ml) and left on filter over night and dried at 40° C. under vacuum until constant weight to give white crystalline product (98.5% area purity by HPLC). The compound so-obtained was slurried in water (50 ml) at ambient temperature for 2 hours. The solid was filtered, washed with $H_2O$ (20 ml) and left on filter overnight and dried at 40° C. under vacuum to give crystalline product.

Example 10

Preparation of TDMV from DDMV in DMA

DDMV.HCl (10 g, 35 mmol), $K_2CO_3$ (5.1 g, 38.4 mmol), Thiophenol (6.2 ml, 52.5 mmol) and DMA (20 ml) were charged in a 100 ml flask equipped with mechanical stirrer, condenser and nitrogen inlet, and heated in a sand bath. The temperature of the reaction mixture was about 110° C.±10° C. for 3 hours. The reaction mixture was cooled to 90° C. and $H_2O$ (50 ml) was added dropwise inducing precipitation. The slurry was cooled to 25° C. and stirred for about 4 hours. The solid was filtered, washed with $H_2O$ (20 ml) and left on filter overnight (95% area purity by HPLC). The compound so-obtained was slurried in water (50 ml) at ambient temperature for 2 hours, filtered, washed with $H_2O$ (20 ml) dried at 40° C. under vacuum to give crystalline product.

Example 11

Preparation of TDMV from DDMV with $Na_2S$ in NMP

DDMV.HCl (81.36 g, 284 mmol), $Na_2S$ (40.0 g, 313 mmol), mmol) and NMP (165 ml) were charged in a 500 ml reactor equipped with mechanical stirrer, condenser dean stark and nitrogen inlet The reaction mixture was heated to 185° C. The reaction mixture was stirred at 185° C. for 8 hours. The reaction mixture was cooled to 90° C. succinic acid (20 g 169 mmol) in $H_2O$ (500 ml) was added dropwise inducing precipitation. The slurry was cooled to 25° C. and stirred overnight. The solid was filtered, washed with $H_2O$ (2×80 ml) and dried overnight at 50° C. under vacuum to get TDMV (96.91% area purity by HPLC— yield 80%).

Example 12

Preparation of O-Desmethylvenlafaxine

TDMV (0.2 g, 0.85 mmol) was dissolved in methanol. Formalin solution (0.4 ml, 5 mmol) was added and the resulting solution was cooled in an ice bath. To the cold solution, $NaBH_4$ (65 mg, 1.7 mmol) was added. After 15 min a sample was analyzed by HPLC, and determined to contain 85% ODV by HPLC area percent.

Example 13

Preparation of O-Desmethylvenlafaxine

TDMV (0.2 g, 0.85 mmol) was dissolved in acetic acid (1 ml). Formalin solution (1.5 ml, 17 mmol) was added to the solution and the solution was cooled in an ice bath. To the cold solution $NaBH(OAc)_3$ (65 mg, 1.7 mmol) was added, forming a slurry that could not be stirred. Acetic acid (1 mL) was added to dilute the slurry. After 15 min, a sample was analyzed by HPLC and determined to contain 36% ODV by HPLC area percent.

Example 14

Preparation of O-Desmethylvenlafaxine

TDMV (0.2 g, 0.85 mmol) was dissolved in dimethylsulfoxide (2.5 ml). The resulting solution was cooled in an ice bath causing its solidification. 1.6 M butyl lithium solution in hexane (1.1 ml, 1.7 mmol) was added, and the temperature was allowed to rise to room temperature. Then methyl iodide (0.13 ml, 2.04 mmol) was added. After 30 minutes, HPLC analysis indicated the presence of ODV.

Example 15

Preparation of O-Desmethylvenlafaxine

TDMV (0.5 g, 2.12 mmol) was suspended in $CH_2Cl_2$. Methyl iodide (0.26 ml, 4.3 mmol) and triethylamine (0.66 ml, 4.73 mmol) were added. The reaction mixture was stirred under nitrogen atmosphere at room temperature for 6 hours. At this stage methyl iodide (0.5 ml) and $NEt_3$ (1.2 ml) were added. The addition caused the temperature to rise. After 16 hours, HPLC analysis indicated the presence of ODV.

What is claimed is:

1. A process for preparing O-desmethylvenlafaxine comprising demethylating didesmethylvenlafaxine to obtain tridesmethyl venlafaxine, and converting said tridesmethyl venlafaxine to O-desmethylvenlafaxine.

2. The process of claim 1, wherein the converting step comprises reductive amination of the tridesmethyl venlafaxine to form O-desmethylvenlafaxine.

3. The process of claim 1, wherein the converting step comprises selectively N,N methylating the tridesmethyl venlafaxine with a methylating agent to form O-desmethylvenlafaxine.

4. The process of claim 3, wherein the methylating agent is selected from the group consisting of a methyl halide, and dimethylsulfate.

5. The process of claim 3, wherein the tridesmethyl venlafaxine and the methylating agent are combined with an organic solvent selected from the group consisting of dichloromethane, dimethylsulfoxide, acetonitrile, tetrahydrofliran, diethylether, and hexane.

6. The process of claim 3, wherein the process is carried out under basic conditions.

7. The process of claim 6, wherein the basic conditions are provided by a base selected from the group consisting of butyllithium, triethylamine, and sodium hydride.

8. The process of claim 1, wherein demethylating comprises reacting didesmethylvenlafaxine with a sulfide containing demethylating agent.

9. The process of claim 8, wherein the reaction of didesmethylventalfaxine with the demethylating agent comprises maintaining a mixture of didesmethylvenlafaxine and the demethylating agent in a solvent at an elevated temperature for a sufficient time to form tridesmethyl venlafaxine.

10. The process of claim 9, further comprising: combining didesmethylvenlafaxine, a high boiling point solvent, and the demethylating agent to form a mixture, and heating the mixture to a temperature of from about 100° C. to about 300° C.

11. The process of claim 10, wherein the temperature is from about 140° C. to about 210° C.

12. The process of claim 11, wherein the temperature is from about 155° C. to about 190° C.

13. The process of claim 9, wherein the mixture is maintained at an elevated temperature for a period of about 1 hour to about 12 hours.

14. The process of claim 10, wherein the high boiling point solvent is selected from the group consisting of: toluene, dimethylformamide ("DMF"), dimethylsulfoxide ("DMSO"), N-methyl-2-pyridone, N-methyl-2-pyrrolidone (NMP), 1-methyl-2-pyrrolidinone, dimethylacetamide ("DMA"), polyethylene glycol, Marlotherm, silicon oil, N,N'-dimethylpropyleneurea ("DMPU"), dimethylolethyleneurea ("DMEU"), hexamethylphosphoramide ("HMPA"), diethylformamide ("DEF"), diethyleneamine ("DEA"), morpholine, sulfolane, phenylether and mixtures thereof.

15. The process of claim 14, wherein the high boiling point solvent is polyethylene glycol, NMP or DMA.

16. The process of claim 9, wherein the mixture is heated to a temperature of about 50° C. to about 200° C. under a pressure of about 1 bar to about 10 bar.

17. The process of claim 16, wherein the temperature is about 80° C.

18. The process of claim 8, wherein the sulfide containing demethylating agent is selected from metal sulfides, the sulfide having a valence of −1 or −2, thiolates and thiols.

19. The process of claim 18, wherein the demethylating agent is selected from a mercaptan, a salt of a thioalcohol, and sodium sulfide.

20. The process of claim 19, wherein the demethylating agent is a high molecular weight thiolate or arene thiolate or thiol.

21. The process of claim 20, wherein the demethylating agent is sodium dodecanethiolate or thiophenol.

22. The process of claim 21, wherein the demethylating agent is thiophenol, and further comprising adding a catalyst to the mixture.

23. The process of claim 22, wherein the catalyst is a base catalyst selected from the group consisting of metal carbonates, metal hydrides, metal hydroxides, metal amides, and metal oxides.

24. The process of claim 23, wherein the catalyst is potassium carbonate.

25. The process of claim 2, wherein the reductive amination of tridesmethyl venlafaxine comprises: combining a tridesmethyl venlafaxine and a formaldehyde source with a reducing agent to form O-desmethylvenlafaxine.

26. The process of claim 25, wherein the tridesmethyl venlafaxine is in a solution of a solvent selected from the group consisting of a $C_{1-4}$ alcohol, a $C_{1-6}$ carboxylic acid, a $C_6$-$C_8$ aromatic hydrocarbon, a $C_3$-$C_5$ ketone, NMP, DMF, and mixtures thereof.

27. The process of claim 25, wherein the process is carried out under acidic conditions.

28. The process of claim 27, wherein the process is carried out in the presence of an organic acid.

29. The process of claim 28, wherein the organic acid is formic acid or acetic acid.

30. The process of claim 25, wherein the source of formaldehyde is selected from the group consisting of gaseous formaldehyde, paraformaldehyde, fomalin solution, and trioxane.

31. The process of claim 25, wherein the reducing agent is selected from the group consisting of sodium borohydride, sodium triacetoxy borohydride, and sodium cyanoborohydride.

32. The process of claim 25, further comprising cooling the mixture of tridesmethyl venlafaxine and a formaldehyde source to a temperature of less than about 10° C., followed by combining the mixture with a reducing agent.

* * * * *